July 22, 1975 TAKESHI YOICHI YONEMOTO Plant Pat. 3,745
CARNATION PLANT
Filed July 3, 1974
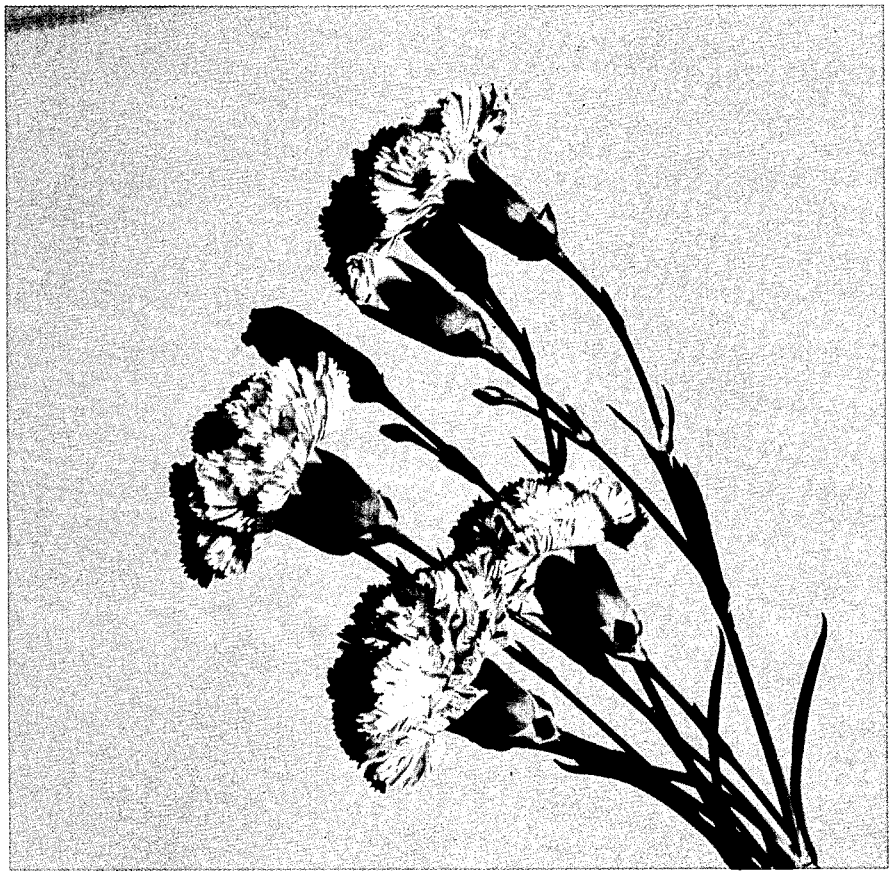

United States Patent

Plant Pat. 3,745
Patented July 22, 1975

3,745

CARNATION PLANT

Takeshi Yoichi Yonemoto, 1328 Henderson Ave., Santa Clara, Calif. 95051

Filed July 3, 1974, Ser. No. 485,383
Int. Cl. A01h *5/00*
U.S. Cl. Plt.—70 1 Claim

ABSTRACT OF THE DISCLOSURE

A new variety of carnation plant originating as a sport of the variety Gayety (unpatented) distinguished by the miniature size of its well formed flowers and the red striped, white bodied flower petals which provide a "peppermint ice cream" appearance to the fully opened bloom.

*Background of the New Plant*

My new variety of carnation was discovered by me at Santa Clara, Calif., in 1968 among my greenhouse production of plants of the standard variety Gayety and this plant came to my attention for further study because of the very small size of its lovely red striped flowers. My subsequent asexual propagation of this new plant by cuttings of the original plant and by cuttings from successive generations of the plant, at Santa Clara, Calif., has demonstrated that the flowers of this plant are a true miniature of the parent and that the novel features of the new plant are well fixed and hold true from generation to generation.

Commercial scale propagation of this new plant is now being done under my direction at Santa Clara, Calif.

*Description of the Drawing*

This new variety of carnation plant is illustrated by the accompanying drawing which shows the full bloom and several stages of its opening as well as the color characteristics of the flower as nearly true as it is reasonably possible to reproduce by conventional photographic procedures.

*Description of the New Plant*

The following is a description of my new variety of carnation plant with the color designations according to the RHS Colour Chart of The Royal Horticultural Society of London, England.

THE PLANT

Origin: Sport.
Parentage: Gayety (unpatented).
Classification:
- Botanic: *Dianthus caryophyllus.*
- Commercial: Greenhouse carnation for production of cut flowers.

Form: Erect and free branching.
Height: About three feet.
Growth: Vigorous and rapid, reaching blossom stage in four months, with strong generally upright stems.

Foliage: Typical of Sim varieties with nine leaves per stem.
- Shape of Leaf: Linear-lanceolate with an acuminate apex and entire margin.
- Color: Light Green.
- Aspect: Glossy.
- Petioles: None. The leaf is decurrent and amplexicaul.

THE BUD

Form: Long—ovoid at time of opening.
Size: About ¾ inch long at first opening.
Opening Rate: Normal for Sim varieties.
Flower Color: When sepals first divide—White edged with red.
- When petals begin to unfurl—White with streaks of red (RHS 45–C).

Sepals: Spear shaped and stand up.
Calyx: Cup shaped with upright segments.
- Aspect: Smooth and shiny.
- Splitting: None.

THE FLOWER

Blooming Characteristics: Perennial and profusely.
Size of Bloom: Small—1½ inch in diameter; ¾ inch in depth.
Borne: Several to each main stem.
Shape: Generally flat with medium high center.
Petalage: 38 to 40 petals in close imbricate arrangement.
- Color: White petal body with broad stripes of red (RHS 45–C) extending to outer end of petal.
- Texture: Soft.
- Appearance: Satiny.

Peduncle: About ½ to ¾ inch long. Sturdy and upright.
Lasting Quality: 2½ weeks as a cut flower.

REPRODUCTIVE ORGANS

Stamens:
- Anthers: Length—⅛ inch. 12 in number.
- Filaments: 1 1/16 inch long. Color: Off-White.
- Pollen: Color—Yellow.

Pistils: 2 in number, each ¾ inch long.
- Stigmas: Color—Yellow.

Ovary: Upright, egg shaped, ⅝ inch long and ⅜ inch wide.

I claim:

1. A new and distinct variety of carnation plant, substantially as herein shown and described, characterized by its small red-on-white flowers, which are miniatures of those of its parent variety, by its profuse year around production of blossoms, and by the long lasting quality of the blossoms as cut flowers.

No references cited.

ROBERT E. BAGWILL, Primary Examiner